United States Patent
Abt et al.

(10) Patent No.: US 11,351,057 B2
(45) Date of Patent: Jun. 7, 2022

(54) LOW FRICTION TROCAR VALVE

(71) Applicant: Alcon Inc., Fribourg (CH)

(72) Inventors: Niels Alexander Abt, Winterthur (CH); Reto Grueebler, Greifensee (CH); Timo Jung, Winterthur (CH); Niccolo Maschio, Winterthur (CH)

(73) Assignee: Alcon Inc., Fribourg (CH)

( * ) Notice: Subject to any disclaimer, the term of this patent is extended or adjusted under 35 U.S.C. 154(b) by 349 days.

(21) Appl. No.: 16/561,137

(22) Filed: Sep. 5, 2019

(65) Prior Publication Data

US 2020/0085615 A1 Mar. 19, 2020

Related U.S. Application Data

(60) Provisional application No. 62/732,305, filed on Sep. 17, 2018.

(51) Int. Cl.
*A61F 9/007* (2006.01)

(52) U.S. Cl.
CPC .................... *A61F 9/007* (2013.01)

(58) Field of Classification Search
CPC .......... A61M 2039/0633; A61M 39/06; A61M 2039/0686; A61M 2039/0626
See application file for complete search history.

(56) References Cited

U.S. PATENT DOCUMENTS

| | | | |
|---|---|---|---|
| 5,256,149 A | 10/1993 | Banik | |
| 5,312,363 A | 5/1994 | Ryan | |
| 5,545,150 A | 8/1996 | Danks | |
| 5,603,702 A * | 2/1997 | Smith | A61B 17/3462 251/149.1 |
| 5,693,031 A | 12/1997 | Ryan | |
| 5,697,947 A | 12/1997 | Wolf | |
| 5,762,314 A * | 6/1998 | Williams | F16K 7/17 251/25 |
| 6,161,571 A * | 12/2000 | Taylor | G05D 16/16 137/488 |
| 6,610,031 B1 * | 8/2003 | Chin | A61M 39/045 604/167.04 |
| 7,846,134 B1 | 12/2010 | Nadolski | |
| 8,109,911 B2 | 2/2012 | Taylor | |
| 8,147,457 B2 * | 4/2012 | Michael | A61B 17/3462 604/167.06 |
| 8,277,418 B2 | 10/2012 | Lopez | |
| 8,343,106 B2 | 1/2013 | Lopez | |
| 8,679,064 B2 | 3/2014 | Lopez | |
| 9,198,797 B2 | 12/2015 | Kerns | |
| 9,265,899 B2 | 2/2016 | Albrecht | |
| 9,393,042 B2 * | 7/2016 | Hart | A61B 17/3462 |

(Continued)

FOREIGN PATENT DOCUMENTS

| | | |
|---|---|---|
| EP | 1671597 A1 | 6/2006 |
| WO | WO2016186905 A1 | 11/2016 |

*Primary Examiner* — Scott J Medway

(57) ABSTRACT

Certain aspects of the present disclosure provide a low friction trocar valve comprising a set of sheets arranged circularly and defining an entry point for the insertion of an instrument. In certain aspects, each sheet of the trocar valve's set of sheets comprises areas that overlap with two adjacent sheets. The trocar valve is formed in an opening of a valve housing coupled to or formed as part of a trocar cannula to provide a sealing mechanism for preventing the escape of pressurized fluids from the trocar cannula.

20 Claims, 5 Drawing Sheets

(56) References Cited

U.S. PATENT DOCUMENTS

| | | | |
|---|---|---|---|
| 2004/0230161 A1* | 11/2004 | Zeiner | A61B 17/3498 604/167.06 |
| 2005/0096605 A1* | 5/2005 | Green | A61M 39/06 604/246 |
| 2005/0131349 A1* | 6/2005 | Albrecht | A61B 17/3496 604/167.06 |
| 2006/0089526 A1 | 4/2006 | Chen | |
| 2008/0312662 A1 | 12/2008 | Hickingbotham | |
| 2009/0192493 A1* | 7/2009 | Meng | A61M 5/46 604/513 |
| 2009/0234293 A1* | 9/2009 | Albrecht | A61B 17/3462 604/167.02 |
| 2010/0057009 A1* | 3/2010 | McQueen | A61M 39/0613 604/164.03 |
| 2010/0063364 A1* | 3/2010 | Bonadio | A61B 17/3423 600/208 |
| 2010/0074775 A1* | 3/2010 | Yamamoto | F04B 43/046 417/413.2 |
| 2010/0204655 A1* | 8/2010 | Melsheimer | A61M 39/06 604/167.03 |
| 2010/0280437 A1* | 11/2010 | Murr | A61B 17/34 604/26 |
| 2011/0087159 A1* | 4/2011 | Parihar | A61B 17/34 604/26 |
| 2012/0310165 A1 | 12/2012 | Hart | |
| 2014/0128775 A1* | 5/2014 | Andreae | A61B 5/1405 600/581 |
| 2019/0053825 A1 | 2/2019 | Ochoa | |
| 2019/0059938 A1* | 2/2019 | Holsten | A61B 17/3462 |
| 2019/0059944 A1 | 2/2019 | Holsten | |
| 2019/0374248 A1 | 12/2019 | Gruebler | |
| 2019/0374249 A1 | 12/2019 | Abt | |
| 2020/0337723 A1* | 10/2020 | Vaccarella | A61B 17/3439 |

* cited by examiner

LOW FRICTION TROCAR VALVE

PRIORITY CLAIM

This application claims the benefit of priority of U.S. Provisional Patent Application Ser. No. 62/732,305 titled "Low Friction Trocar Valve," filed on Sep. 17, 2018, whose inventors are Niels Alexander Abt, Reto Grueebler, Timo Jung and Niccolo Maschio, which is hereby incorporated by reference in its entirety as though fully and completely set forth herein.

INTRODUCTION

The present disclosure relates generally to trocars and more specifically to seals applicable to trocars.

Surgical instruments may be used by surgeons for the dissection and removal of tissue from delicate and restricted spaces in the human body, such as in eye surgeries (e.g., procedures for removal of the vitreous body, blood, scar tissue, or the crystalline lens). A surgeon may use several surgical instruments during the procedure, which may require that these instruments be inserted into and removed out of the incision. This repeated removal and insertion may cause trauma to the eye at the incision site. To address this concern, trocar devices were developed and are now commonly used.

A trocar device includes a narrow trocar cannula that may be inserted into an incision in the body part. Surgical instruments can be inserted into the body part through the trocar cannula and the trocar cannula may protect the incision sidewall from repeated contact by the instruments. In some cases, trocar devices are introduced into regions of the body which include material or fluid under pressure. The fluid may be a liquid, such as blood, or a gas, such as insufflation gas. When a trocar device is used for performing eye-related surgeries, the fluid may include vitreous humour. The eye, being a pressurized globe, may expel vitreous out of the trocar cannula when the trocar device is inserted into the eye. In these examples, it is desirable to enable the insertion of the trocar device into the body part while preventing the pressurized fluid from escaping.

To prevent the loss of pressurized fluids through the trocar cannula, the trocar cannula may be connected to a seal housing at the distal end of the trocar device which includes a seal. Together, the trocar cannula and the seal housing form a working channel through which various instruments can be inserted to access the body part. A seal commonly includes a valve which seals the working channel when an instrument is inserted and after the instrument is removed. Currently, trocar valves are constructed out of materials that create high friction with surgical instruments that are inserted into the valve. The geometrical arrangement of existing valves also contributes to the high friction between the valve and surgical instruments. In some cases, this is because the valve or the valve's flaps have a high amount of contact with a surgical instrument that is inserted into the valve. Friction can cause the valve's sealing components to fold or otherwise be compromised during the insertion and removal of the surgical instrument into and out of the valve. This folding results in a sudden move or jerking of the surgical instrument, which may disturb the surgeon. The folding and the friction also cause a slip-stick motion that provides an inconsistent feedback to a surgeon who is operating with the instrument. Even more, the friction between the instrument and the valve's sealing components may make it very difficult to insert and remove an instrument into and out of the valve, which may result in a more cumbersome and less efficient procedure.

BRIEF SUMMARY

The present disclosure relates to trocar devices and valve assemblies for use with trocar devices. Certain embodiments provide a trocar device comprising a trocar cannula, a valve housing connectable to an end of the trocar cannula, and a valve formed in an opening of the valve housing. In certain embodiments, the valve comprises a set of sheets arranged circularly and defining an entry point for insertion of an instrument, wherein each sheet of the set of sheets comprises areas that overlap with two adjacent sheets of the set of sheets.

Certain embodiments provide a trocar valve comprising a set of sheets arranged circularly and defining an entry point for insertion of an instrument, wherein each sheet of the set of sheets comprises areas that overlap with two adjacent sheets of the set of sheets.

Certain embodiments provide a trocar valve assembly connectable to a trocar cannula, the trocar valve assembly comprising a valve housing and a valve coupled to the valve housing, the valve comprising a set of sheets arranged circularly and defining an entry point for insertion of an instrument, wherein each sheet of the set of sheets comprises areas that overlap with two adjacent sheets of the set of sheets.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide a trocar device having a low friction trocar valve for preventing the escape of pressurized fluid from a body part after the insertion of the trocar device into the body part (e.g., of a human, animal, etc.).

As described above, existing trocars comprise trocar valves that are constructed out of material that shows high friction to surgical instruments. More specifically, trocar valves are made out of elastomer materials, such as silicone elastomers. Silicone elastomers have a high friction coefficient to stainless steel, which is the material that surgical instruments are generally constructed with. In addition to the material, existing silicon silicone elastomer valve's geometrical arrangement includes an opening which results in circumferential contact with an inserted surgical instrument. This circumferential contact increases the surface area of contact and therefore contributes to the friction between the silicone elastomer valve and a surgical instrument.

Friction causes the silicone valve's flaps to fold in the direction of the surgical instrument's movement. As the flaps of the silicone elastomer valve fold, the pressure of the flaps acting on the instrument increases. This folding action causes a small jump as well as a slip-stick motion that may disturb and provide inconsistent feedback to a surgeon as mentioned above. In addition, the increased friction between the instrument and the silicone valve may impede the surgeon's ability to efficiently and easily insert and remove the instrument in and out of the silicone valve. Accordingly, certain embodiments described herein relate to providing a trocar valve constructed with a material and a geometrical arrangement that result in the trocar valve having a low friction with surgical instruments while also preventing the escape of pressurized fluids.

Figure 1:
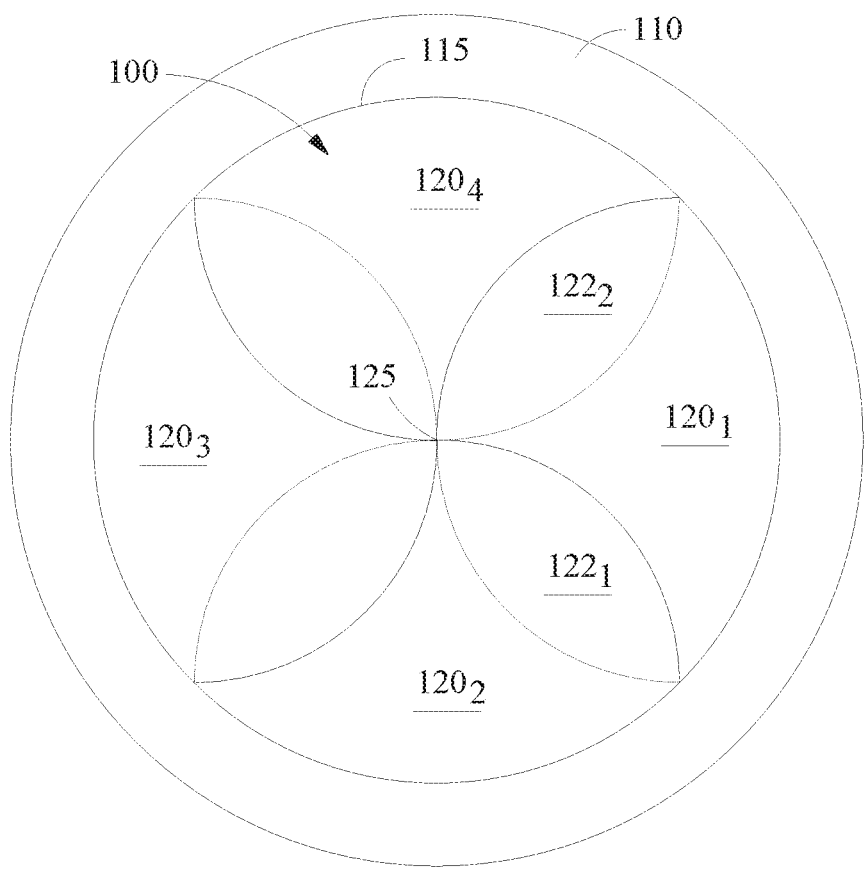
FIG. 1 illustrates a top view of an exemplary low friction trocar valve formed in an opening of a valve housing, according to some embodiments.

FIG. 1 illustrates a top view of an exemplary low friction trocar valve 100 formed in an opening 115 of a valve housing 110. As shown, trocar valve 100 comprises sheets 120 that are arranged circularly within valve housing 110 and define a central entry point 125 for the insertion of a surgical instrument. In the example of FIG. 1, the valve includes four sheets $120_1$-$120_4$, each of which includes areas that overlap with two adjacent sheets. For example, sheet $120_1$ comprises areas $122_1$ and $122_2$. As shown, area $122_1$ overlaps with sheet $120_2$ while area $122_2$ overlaps with sheet $120_4$. In some embodiments, the arrangement of sheets 120 is similar to the arrangement of an aperture of a camera. As shown in FIG. 1, each sheet 120 comprises an area that is placed underneath an adjacent sheet 120 and another area that is placed above a different adjacent sheet. For example, area $122_1$ of sheet $120_1$ is placed underneath sheet $120_2$ while area $122_2$ of sheet $120_1$ is placed above sheet $120_4$.

As shown, sheets 120 do not overlap at the center of trocar valve 100, thereby forming entry point 125 to allow for the insertion of a surgical instrument. The geometrical arrangement of sheets 120 provides a seal at entry point 125, even when a surgical instrument is not inserted into trocar valve 100. The seal is formed where sheets $120_1$-$120_4$ all intersect, thereby, closing or at least significantly minimizing any opening at entry point 125 to prevent the escape of pressurized fluids.

After a trocar device that includes trocar valve 100 is inserted into a body part, and before the insertion of a surgical instrument into trocar valve 100, the internal pressure of the body part's fluid (e.g., internal pressure of the eye) exerts force on sheets 120. This force increases the friction between sheets 120 and also presses them together at the center, which results in closing any potential opening at entry point 125. In other words, in response to the internal pressure of the body part's fluid, sheets 120 create a locking effect at the center that helps prevent the escape of the body part's fluid. Accordingly, the geometrical arrangement of trocar valve 100 enables trocar valve 100 to function as a more effective and reliable seal than existing trocar valves.

The shape of sheets 120 at entry point 125 and the overall geometrical arrangement of trocar valve 100 also result in a low friction between trocar valve 100 and a surgical instrument. The curved shape of sheets 120 at entry point 125 results in minimum contact between a surgical instrument and each sheet 120. More specifically, it is only the tip of each curved sheet 120 that contacts the inserted surgical instrument. In contrast, existing silicone elastomer valves have circumferential contact with a surgical instrument at the point of insertion. As a result of the lowered friction between trocar valve 100 and the surgical instrument, sheets 120 are less likely to fold in the direction of a surgical instrument's upward and downward movements.

In addition to the geometrical arrangement of trocar valve 100, in some embodiments, trocar valve 100 comprises material that also contributes significantly to the reduction of the friction described above. In some embodiments, sheets 120 comprise material with a low friction-coefficient. For example, the friction-coefficient of the material of sheets 120 to surgical instruments may be lower than the friction-coefficient of silicone elastomer to surgical instruments. In cases where the surgical instrument being used is manufactured with stainless steel (e.g., polished stainless steel), sheets 120 may comprise material with a friction-coefficient to stainless steel that is lower than the friction-coefficient of silicone elastomers (or any other elastomer material) to stainless steel.

In some embodiments, sheets 120 may comprise a polyimide film while, in some other embodiments, sheets 120 may comprise a glass film. Also, in some embodiments, sheets 120 may comprise Polytetrafluoroethylene (PTFE) material and, in some other embodiments, sheets 120 may comprise Polyether ether ketone (PEEK) material. Any combination of the materials described above may also be used.

Although the trocar valve 100 of FIG. 1 comprises four sheets 120, in some other embodiments, a larger number of sheets are used to form a trocar valve with a similar geometrical arrangement. For example, in some embodiments, eighteen sheets may be used to construct a trocar valve. In another example, ten sheets may be used to construct a trocar valve. In some other embodiments, a fewer number of sheets are used to form a trocar valve with a similar geometrical arrangement. For example, in some embodiments, three sheets may be used to construct a trocar valve.

Figure 2:
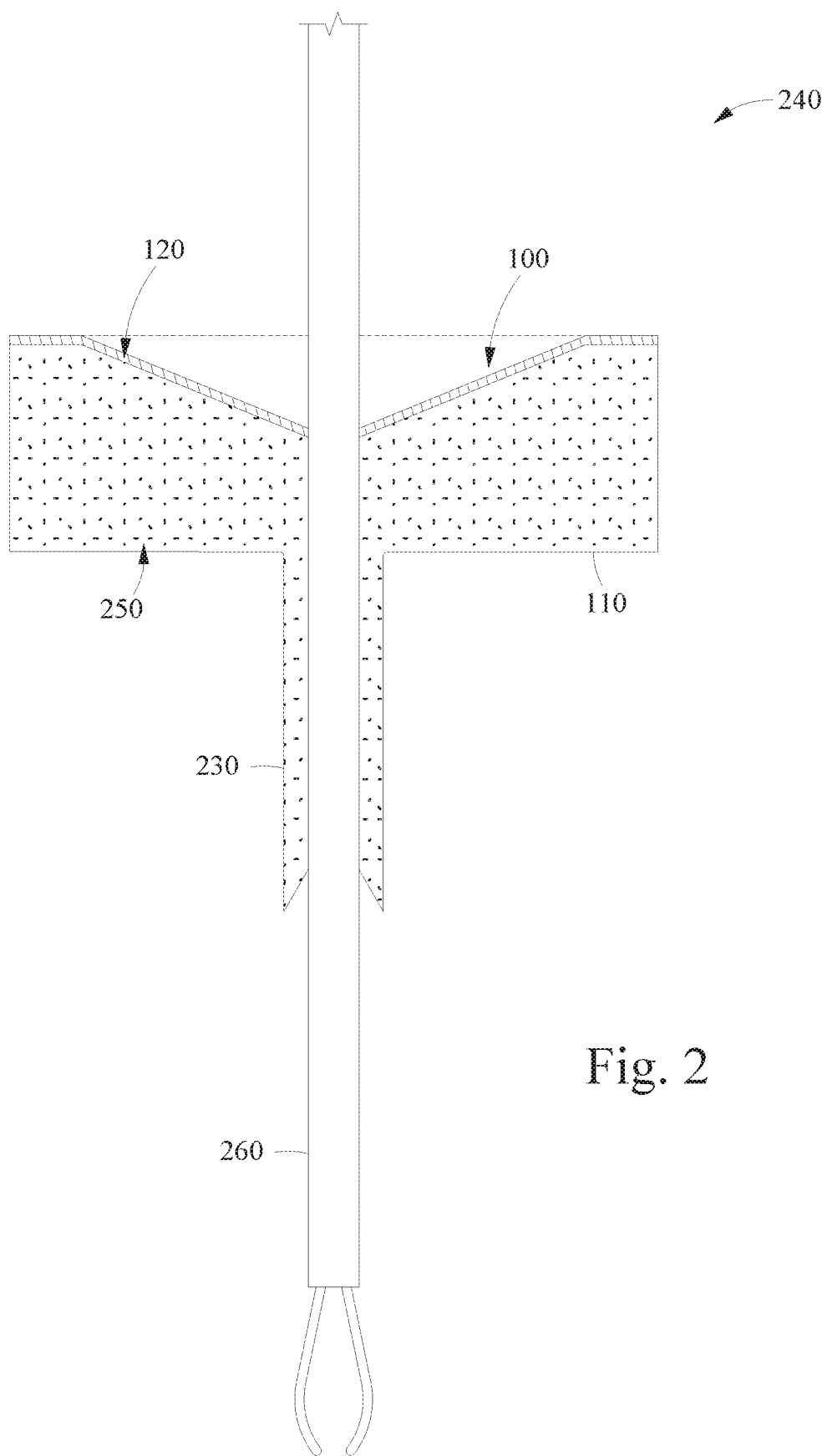
FIG. 2 illustrates a cross sectional view of an exemplary trocar device and a surgical instrument inserted into the trocar cannula, according to some embodiments.

FIG. 2 illustrates a cross sectional view of a trocar device 240 and a surgical instrument 260, inserted into trocar device 240. Trocar device 240 comprises a trocar cannula 230 and trocar valve assembly 250, including valve housing 110 and trocar valve 100. In the example of FIG. 2, trocar valve assembly 250 is formed as part of trocar cannula 230. As shown, trocar cannula 230 has one end that is inserted into a body part and another end that comprises valve housing 110 for housing trocar valve 100.

Valve housing 110 also provides a stopping mechanism by functioning as an overcap that prevents trocar device 240 from being inserted all the way into a body part. As shown in FIG. 2, surgical instrument 260 is inserted into trocar valve 100 through the entry point of trocar valve 100 (e.g., entry point 125 in FIG. 1), and trocar cannula 230. In response to the insertion of surgical instrument 260, sheets 120 of trocar valve 100 transform into a funnel-like structure. When the surgeon starts pulling surgical instrument 260 out of trocar device 240, an outward movement of sheets 120 may be prevented by a cap that may be placed on top of trocar valve 100.

FIG. 2 illustrates one embodiment of trocar device 240. In some other embodiments, instead of being formed as a part of trocar cannula 230, trocar valve assembly 250 is a separate component of trocar device 240 that is connectable to trocar cannula 230. In such embodiments, trocar valve assembly 250 and trocar cannula 230 may be coupled together such that trocar valve assembly 250 is prevented from rotating in relation to trocar cannula 230. In some embodiments, trocar valve assembly 250 and trocar cannula 230 may be coupled together using a threaded connection. In some embodiments, trocar valve assembly 250 and trocar cannula 230 may be coupled together using a snap connection mechanism.

Figure 3A:
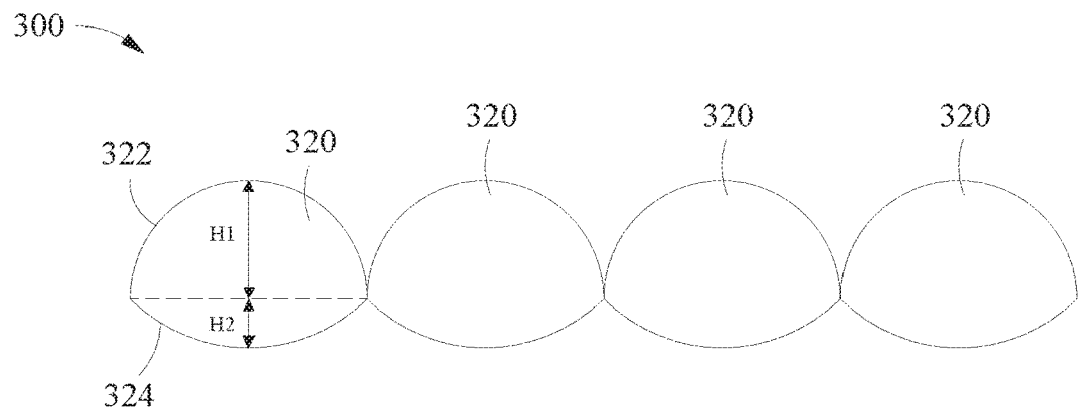
FIG. 3A illustrates an exemplary corrugated strip comprising a number of sheets, according to some embodiments.

FIG. 3A shows an exemplary corrugated strip 300 comprising sheets 320. Corrugated strip 300 is formed by cutting a strip of material (e.g., polyimide film, glass film, PTFE material, or PEEK material) to form sheets 320 which are attached together. As shown in FIG. 3A, each sheet 320 comprises arc 322 and arc 324. A dotted line is used to distinguish between the two arcs 322 and 324 of the first sheet 320 of FIG. 3A. Arc 322 is a half circle with an arc length that is larger than the arc length of arc 324. In some embodiments, a diameter of the valve 100 (e.g., diameter of outer circle in FIG. 3*b*) may be approximately in a range of 0.6 millimeters (mm) to 2.75 mm. Other diameters are also contemplated (e.g., different ophthalmic cannula gauge sizes or cannulas for different body parts may be larger or smaller than these dimensions.) In some embodiments, this may result in a length of the dashed line (between arc 322 and arc 324 in FIG. 3A) for one pedal being approximately in a range of 0.42 mm to 1.94 mm. Other lengths are also contemplated (e.g., approximately in a range of 0.3 mm to 2.5 mm). In some embodiments, height (H1) may be approximately in a range of 0.21 mm to 0.97 mm. Other heights (H1) are also contemplated (e.g., approximately in a range of 0.15 mm to 1.25 mm). In some embodiments, height (H2) may be approximately in a range of 0.09 mm to 0.97 mm. Other heights (H1) are also contemplated (e.g., approximately in a range of 0.062 mm to 0.52 mm). In some embodiments, the ratio of H1 to H2 (in FIG. 3A) may be approximately 1 to 0.4. Other ratios of H1 to H2 are also contemplated.

Figure 3B:
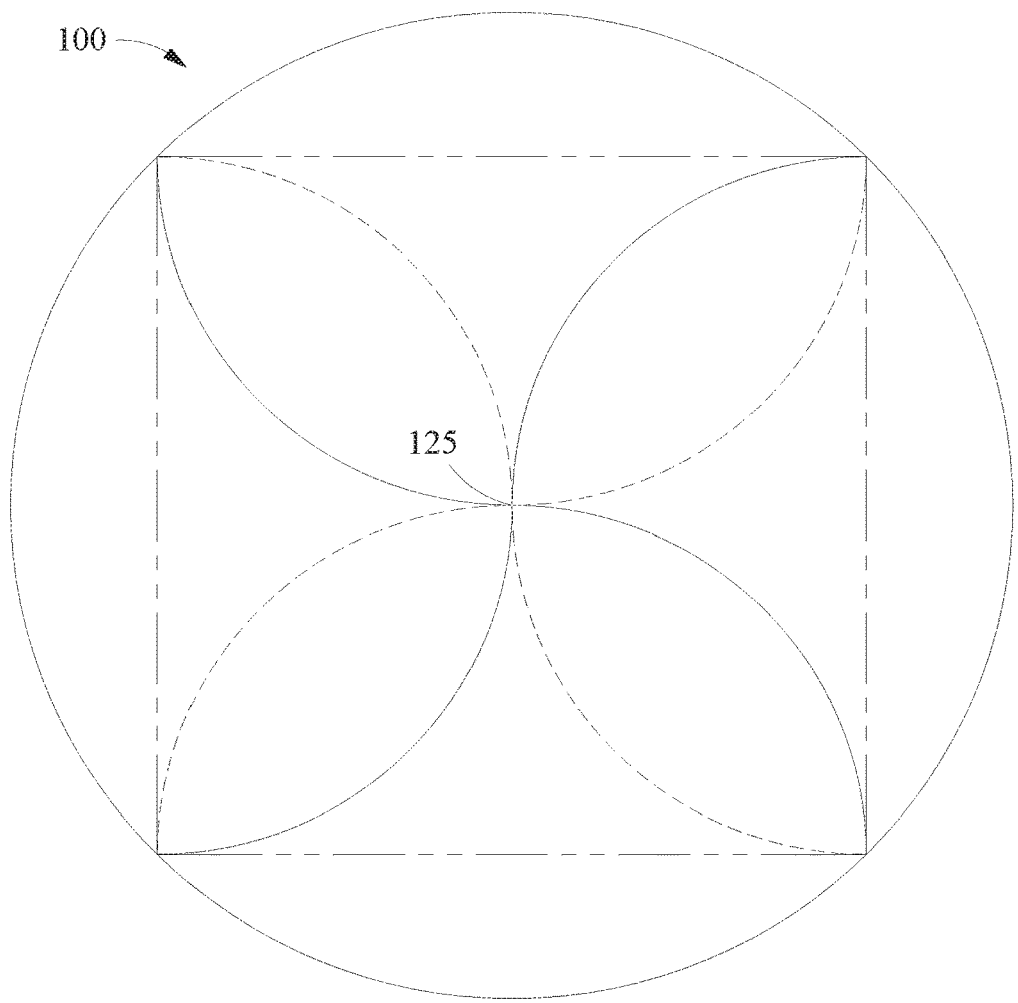
FIG. 3B illustrates an exemplary trocar valve formed using the corrugated strip of FIG. 3A, according to some embodiments.

To form trocar valve 100 with the geometrical arrangement shown in FIG. 3B, corrugated strip 300 is furled. FIG. 3B illustrates an exemplary trocar valve 100 formed as a result of furling sheets 320 of FIG. 3A. Trocar valve 100 of FIG. 3B is then clamped onto the valve housing (e.g., valve housing 110 shown in FIGS. 1-2). In some embodiments, trocar valve 100 may be attached to valve housing 110 using adhesive material. In some embodiments, trocar valve 100 is clamped in between valve housing 110 and a cap (e.g., cap 415 shown in FIGS. 4A-4B).

Figure 4A:
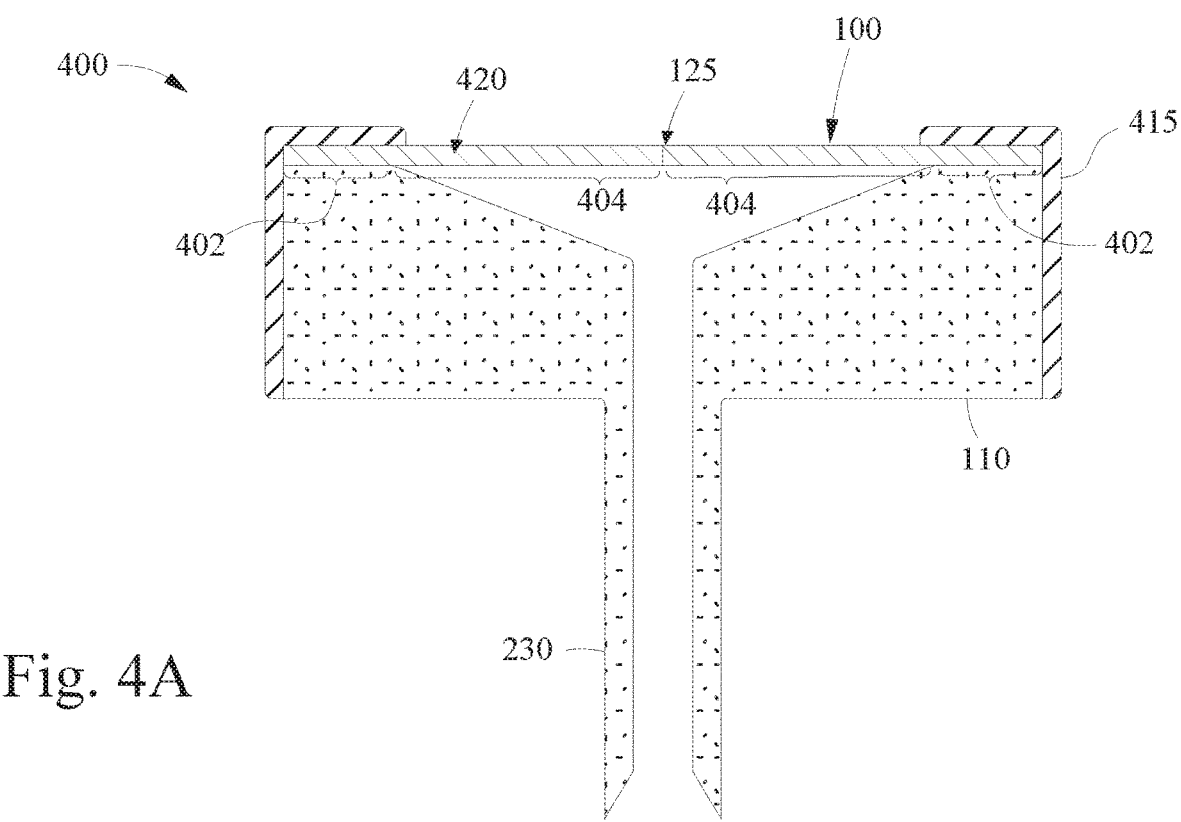
FIG. 4A illustrates an exemplary cross sectional view of a trocar, according to some embodiments.

FIG. 4A illustrates an exemplary cross sectional view of trocar device 400. As shown, trocar valve 100 is clamped between cap 415 and valve housing 110. As described above, cap 415 constrains trocar valve 100 (i.e., holds trocar valve 100 in place) and also prevents an outwards bending of sheets 420 during the removal (i.e., upward movement) of an instrument. Trocar valve 100 comprises outer edges 402 and inner edges 404. Outer edges 402 are parts that are clamped between cap 415 and valve housing 110 and, thereby, hold trocar valve 100 in place and prevent trocar valve 100 from rotating, etc. Inner edges 404 are parts that deflect or move in response to the movements of an instrument that is inserted into trocar valve 100. In certain embodiments, cap 415 may horizontally extend even further along sheets 420 (towards entry point 125) to not only cover the length of outer edges 402 but also a certain portion of inner edges 404. In such aspects, the elongated cap 415 may provide an even better protection against the outwards bending of sheets 420 during the removal of an instrument.

As shown in FIG. 4A, outer edges 402 of the sheets of trocar valve 100 are positioned on the upper surface of the trocar valve 100 and held in place by a cap 415 disposed over the upper surface of the sheets. The sheets extend in a horizontal direction (e.g., at 0°) across the opening of the trocar valve. The rigidity of the material of sheets 420 as well as their overlapping arrangement help ensure that sheets 420 remain horizontally straight, thereby, allowing the innermost edges of the sheets 420 (i.e., tips of inner edges 404) to be in contact at entry point 125.

Figure 4B:
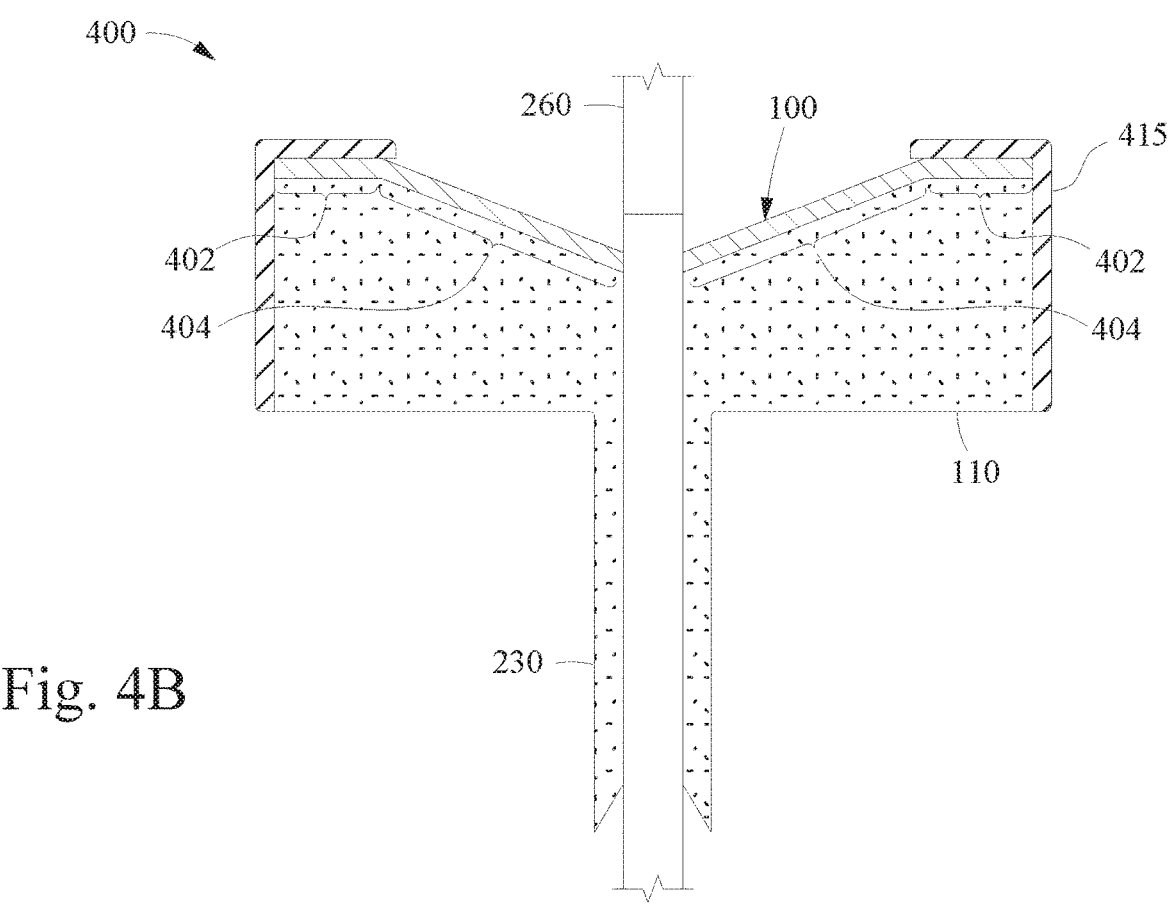
FIG. 4B illustrates exemplary moving parts of a trocar valve being pushed down or moving in the direction of a surgical instrument's insertion into the trocar valve, according to some embodiments.

FIG. 4B illustrates an example of inner edges 404 of trocar valve 100 deflecting in the direction of instrument 260's insertion into trocar valve 100. The outer edges 402 of trocar valve 100 remain stationary in response to an instrument's insertion or removal into and out of trocar valve 100.

Figure 4C:
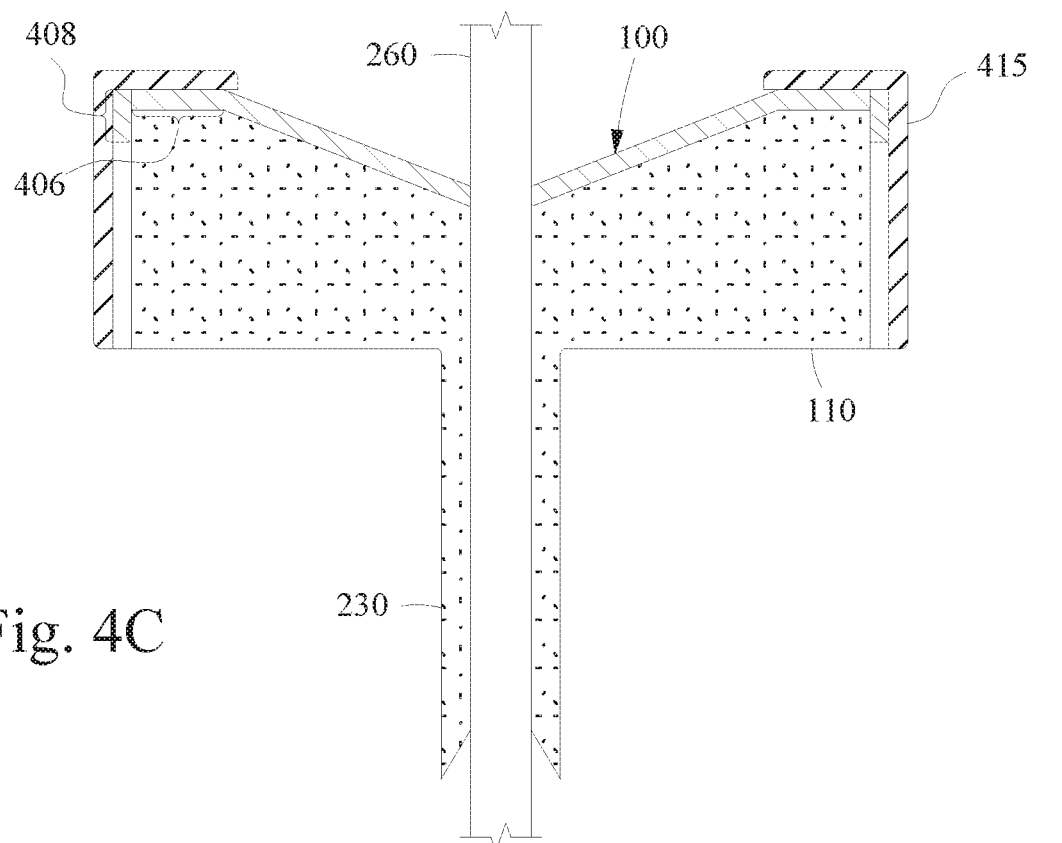
FIG. 4C illustrates an exemplary trocar valve being clamped in between a cap and a valve housing, according to some embodiments.

FIG. 4C illustrates another embodiment of trocar valve 100 in which the valve sheets are clamped between cap 415 and valve housing 110. As shown, trocar valve 100 of FIG. 4C comprises outer edges 406 and 408. Similar to outer edges 402 of FIG. 4A, outer edges 406 of FIG. 4C are horizontally clamped between cap 415 and valve housing 110. In addition to outer edges 406, trocar valve 100 of FIG. 4C also comprises outer edges 408, which are vertically clamped between cap 415 and valve housing 110. Clamping outer edges 408 of trocar valve 100 between cap 415 and valve housing 110 reduces the likelihood of trocar valve 100 detaching from or rotating in relation to valve housing 110.

In other embodiments, trocar valve 100 may comprise more than one layer of sheets. For example, trocar valve 100 may comprise a stack of two or more layers of sheets to provide a labyrinth seal with an additional sealing effect.

Figure 5:
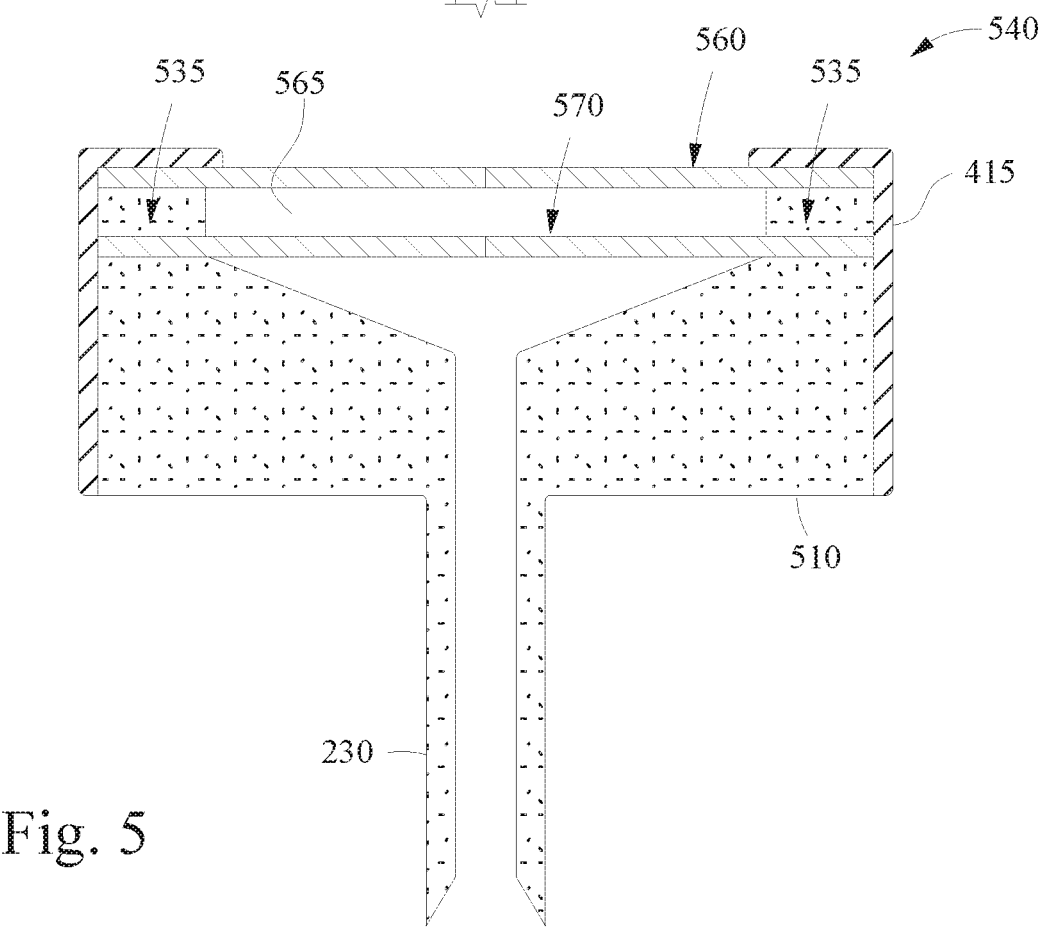
FIG. 5 illustrates an exemplary trocar device comprising a trocar valve with two layers of sheets including a first layer, comprising a first set of sheets, and a second layer, comprising a second set of sheets, according to some embodiments.

FIG. 5 illustrates an exemplary trocar device 540 comprising trocar valve 500 with two layers of sheets including a first layer 560, comprising a first set of sheets, and a second layer 570, comprising a second set of sheets. As shown, first layer 560 and second layer 570 are separated by a gap 565. In the example of FIG. 5, trocar 540 is assembled by first clamping the second layer 570 onto valve housing 510. Subsequently, a component 535 is clamped onto the second layer 570. In some embodiments, component 535 is a ring-shaped component and has the same diameter as the diameter of the first layer 560 and the second layer 570. In some embodiments, first layer 560 and second layer 570 also have the same diameter. In some embodiments, the component 535 comprises the same material as the material used for manufacturing valve housing 510. Trocar device 540 may continue to be assembled by clamping the first layer 560 onto component 535 and, subsequently, clamping cap 415 on top of first layer 560.

Accordingly, a low friction trocar valve is provided for placement in an opening of a valve housing, coupled to or formed as part of a trocar cannula, to prevent the escape of pressurized fluids from the trocar cannula.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. A trocar device comprising:
   a trocar cannula;
   a valve housing connectable to an end of the trocar cannula; and
   a valve formed in an opening of the valve housing, the valve comprising:
   a set of sheets arranged circularly and defining an entry point for insertion of an instrument, wherein each sheet of the set of sheets comprises areas that overlap with two adjacent sheets of the set of sheets;
   wherein each sheet of the set of sheets comprises a half-circle portion with a first arc length and an arc portion with a second arc length, wherein the half-circle portion of each sheet connects to the arc portion of each sheet along a straight line with a length equal to two times the first arc length; and
   wherein, when the set of sheets is arranged circularly, outer perimeters of the arc portions together form an outer circle with a radius equal to the first arc length plus the second arc length.

2. The trocar device of claim 1, wherein the valve housing further comprises a circular cap placed on top of the set of sheets to prevent the set of sheets from folding.

3. The trocar device of claim 1, wherein the valve further comprises:
   an additional set of sheets placed underneath the set of sheets in the valve housing, wherein the additional set of sheets and the set of sheets are separated by a gap, wherein the additional set of sheets is arranged circularly and defining an additional entry point such that each sheet of the additional set of sheets comprises areas that overlap with two adjacent sheets of the additional set of sheets.

4. The trocar device of claim 1, wherein the set of sheets comprises material with a friction-coefficient to stainless steel that is lower than a friction-coefficient of silicone to stainless steel.

5. The trocar device of claim 1, wherein the set of sheets comprises at least one of polyimide film or glass film.

6. The trocar device of claim 1, wherein the set of sheets comprises Polytetrafluoroethylene (PTFE) material.

7. The trocar device of claim 1, wherein the set of sheets comprises Polyether ether ketone (PEEK) material.

8. The trocar device of claim 1, wherein each sheet of the set of sheets is attached to at least another sheet of the set of sheets.

9. The trocar device of claim 1, wherein the valve housing is formed as a part of the trocar cannula.

10. A trocar valve attached to a valve housing, the trocar valve comprising:
    a set of sheets arranged circularly and defining an entry point for insertion of an instrument, wherein each sheet of the set of sheets comprises areas that overlap with two adjacent sheets of the set of sheets;
    wherein each sheet of the set of sheets comprises a half-circle portion with a first arc length and an arc portion with a second arc length, wherein the half-circle portion of each sheet connects to the arc portion of each sheet along a straight line with a length equal to two times the first arc length; and
    wherein, when the set of sheets is arranged circularly, outer perimeters of the arc portions together form an outer circle with a radius equal to the first arc length plus the second arc length.

11. The trocar valve of claim 10, wherein the valve housing is connectable to a trocar cannula or formed as part of the trocar cannula.

12. The trocar valve of claim 10, further comprising:
    a circular cap placed on top of the set of sheets to prevent the set of sheets from folding.

13. The trocar valve of claim 10, wherein the trocar valve further comprises:
    an additional set of sheets placed underneath the set of sheets in the valve housing, wherein the additional set of sheets and the set of sheets are separated by a gap, wherein the additional set of sheets is arranged circularly and defining an additional entry point such that each sheet of the additional set of sheets comprises areas that overlap with two adjacent sheets of the additional set of sheets.

14. The trocar valve of claim 10, wherein the set of sheets comprises material with a friction-coefficient to stainless steel that is lower than a friction-coefficient of silicone to stainless steel.

15. The trocar valve of claim 10, wherein the set of sheets comprises at least one of polyimide film, glass film, a Polytetrafluoroethylene (PTFE) material, or a Polyether ether ketone (PEEK) material.

16. A trocar valve assembly connectable to a trocar cannula, the trocar valve assembly comprising:
    a valve housing; and
    a valve coupled to the valve housing, the valve comprising a set of sheets arranged circularly and defining an entry point for insertion of an instrument, wherein each sheet of the set of sheets comprises areas that overlap with two adjacent sheets of the set of sheets;

wherein each sheet of the set of sheets comprises a half-circle portion with a first arc length and an arc portion with a second arc length, wherein the half-circle portion of each sheet connects to the arc portion of each sheet along a straight line with a length equal to two times the first arc length; and wherein, when the set of sheets is arranged circularly, outer perimeters of the arc portions together form an outer circle with a radius equal to the first arc length plus the second arc length.

17. The trocar valve assembly of claim 16, wherein the trocar valve assembly is formed as part of the trocar cannula.

18. The trocar valve assembly of claim 16, wherein the trocar cannula has a first end and a second end, wherein the first end comprises the trocar valve assembly.

19. The trocar device of claim 1, wherein the half-circle portion and the arc portion of each sheet together form a continuous sheet.

20. The trocar valve of claim 10, wherein the half-circle portion and the arc portion of each sheet together form a continuous sheet.

\* \* \* \* \*